United States Patent
Young

(10) Patent No.: US 8,632,504 B2
(45) Date of Patent: Jan. 21, 2014

(54) DRUG CONTAINER AND DELIVERY MECHANISM

(75) Inventor: Matthew Young, Cambridge (GB)

(73) Assignee: Oval Medical Technologies Limited, Cambridge (GB)

( * ) Notice: Subject to any disclaimer, the term of this patent is extended or adjusted under 35 U.S.C. 154(b) by 21 days.

(21) Appl. No.: 13/202,007

(22) PCT Filed: Feb. 17, 2010

(86) PCT No.: PCT/GB2010/000282
§ 371 (c)(1),
(2), (4) Date: Aug. 17, 2011

(87) PCT Pub. No.: WO2010/094916
PCT Pub. Date: Aug. 26, 2010

(65) Prior Publication Data
US 2011/0301548 A1    Dec. 8, 2011

(30) Foreign Application Priority Data
Feb. 17, 2009  (GB) .................................. 0902645.1

(51) Int. Cl.
*A61M 5/24*  (2006.01)
*A61M 5/28*  (2006.01)
*A61M 5/00*  (2006.01)
*A61M 5/20*  (2006.01)

(52) U.S. Cl.
USPC ............ 604/200; 604/191; 604/135; 604/201

(58) Field of Classification Search
USPC .......... 604/191, 134–137, 200–206, 157, 187
See application file for complete search history.

(56) References Cited

U.S. PATENT DOCUMENTS

| | | | |
|---|---|---|---|
| 3,902,491 A | 9/1975 | Lajus | |
| 4,744,790 A * | 5/1988 | Jankowski et al. | 604/232 |
| 6,343,718 B1 | 2/2002 | Montenieri et al. | |
| 6,406,455 B1 * | 6/2002 | Willis et al. | 604/68 |
| 7,081,107 B2 | 7/2006 | Kito et al. | |
| 2005/0119620 A1* | 6/2005 | Tachikawa et al. | 604/187 |
| 2007/0078392 A1* | 4/2007 | Jessop et al. | 604/122 |

FOREIGN PATENT DOCUMENTS

| | | |
|---|---|---|
| CA | 2585139 A1 | 5/2006 |
| DE | 19925621 A1 | 12/1999 |
| DE | 10102054 A1 | 8/2002 |
| EP | 1459775 A1 | 9/2004 |
| EP | 1530978 A1 | 5/2005 |
| FR | 2227020 A1 | 11/1974 |
| GB | 1471375 | 4/1977 |
| JP | 11033114 A | 7/1977 |
| JP | 2001017546 A | 7/1999 |
| JP | 2001029466 | 2/2001 |
| JP | 2006116223 A | 10/2004 |

* cited by examiner

Primary Examiner — Nicholas Lucchesi
Assistant Examiner — Rebecca E Eisenberg
(74) Attorney, Agent, or Firm — Lando & Anastasi, LLP

(57) ABSTRACT

A device for storing and administering drug includes a housing, a sealing element (3) and a separate low friction plunger (4) which is substantially-permeable to gas over time. The sealing element (3) is typically broken to allow delivery of the drug. The housing (2) may be filled with the drug through an opening other than the opening through which the pusher (13) enters the housing to move the plunger so as to expel the drug during administration to a patient.

21 Claims, 18 Drawing Sheets

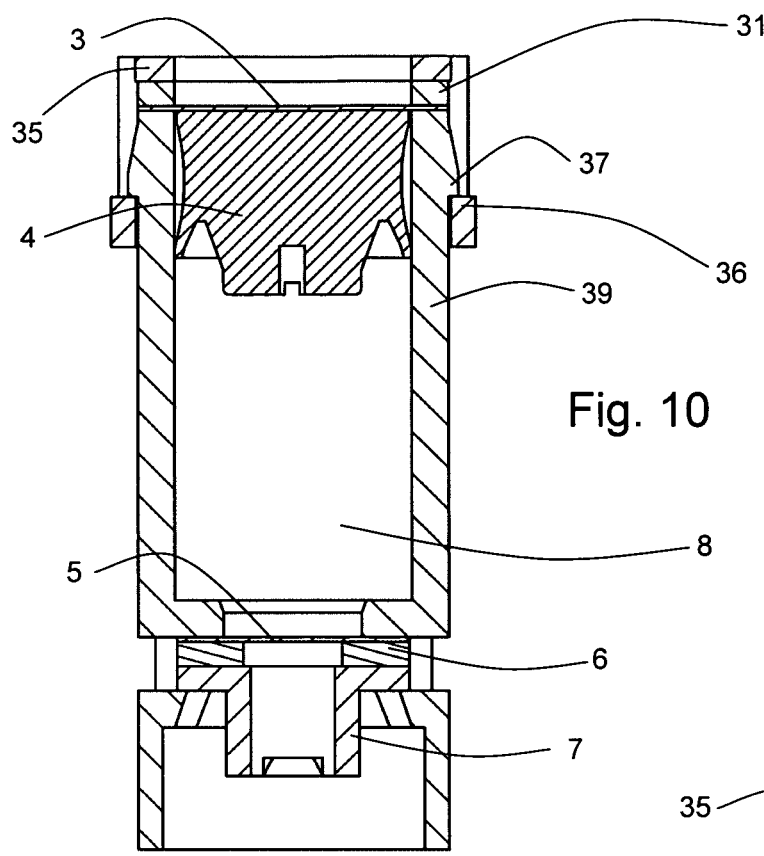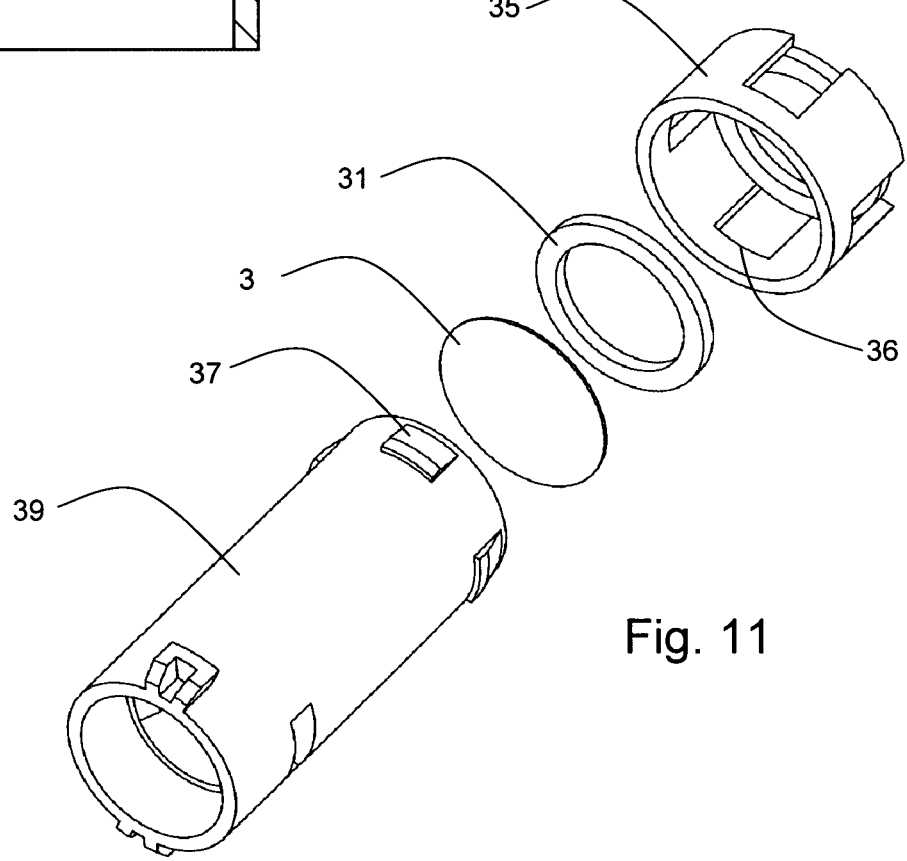
Fig. 10
Fig. 11

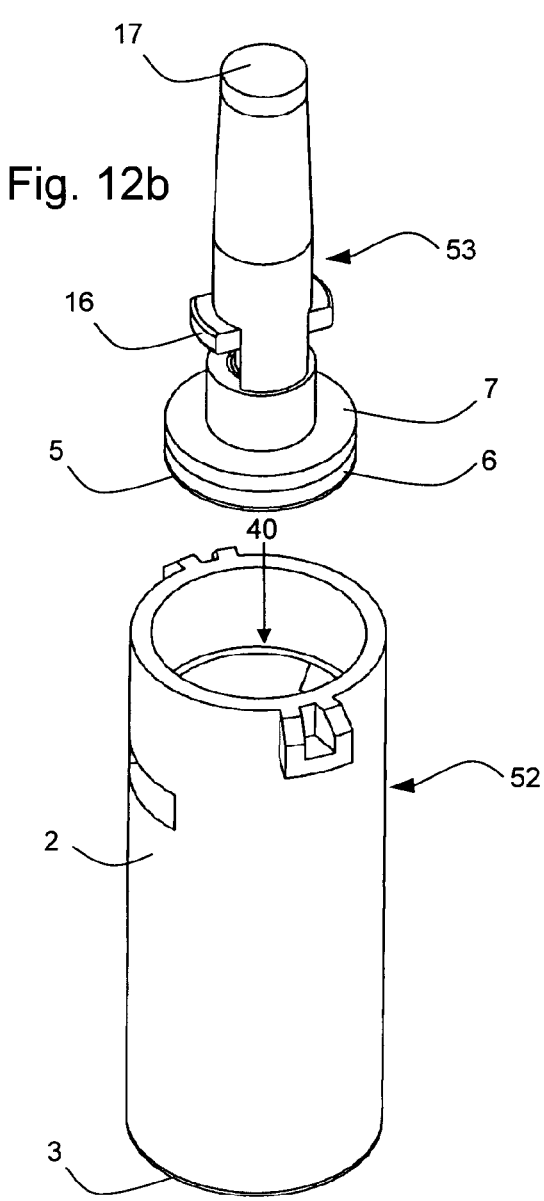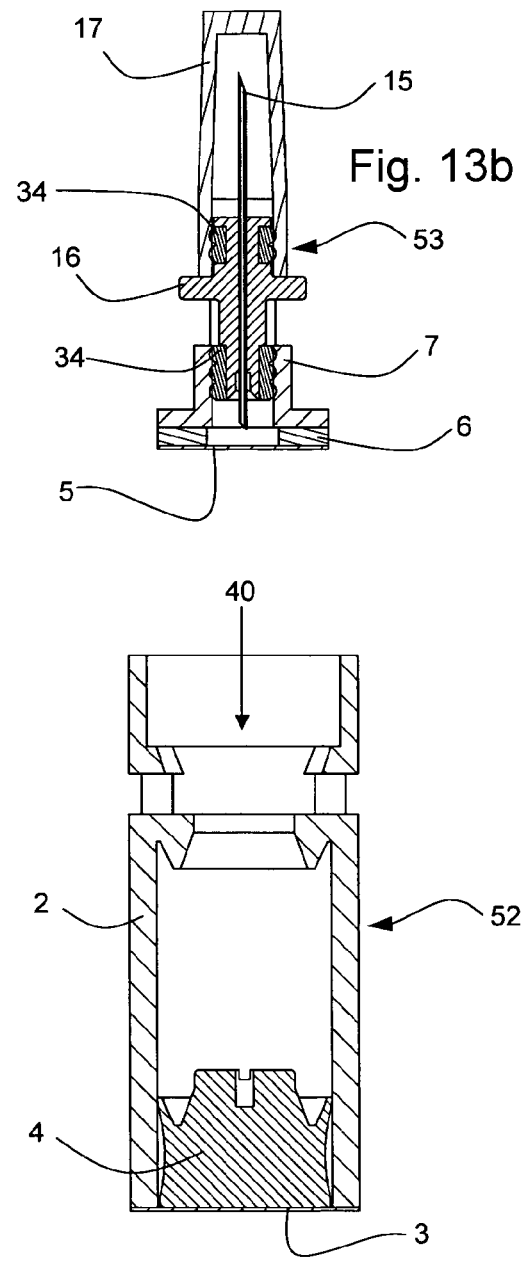

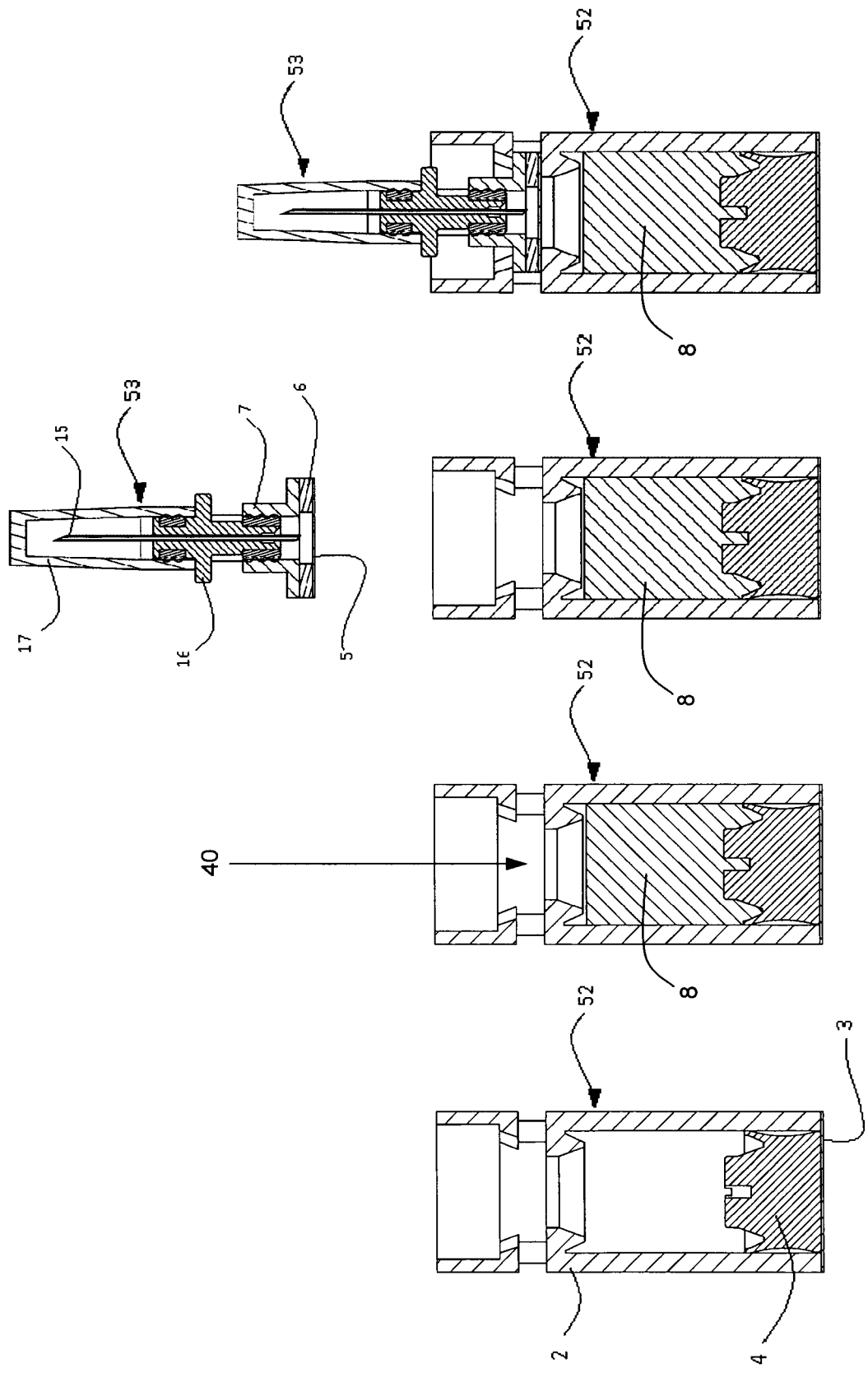

DRUG CONTAINER AND DELIVERY MECHANISM

CROSS-REFERENCE TO RELATED APPLICATION

This application is a continuation of PCT International Patent Application No. PCT/GB2010/000282, entitled Drug Container and Delivery Mechanism, which claims the benefit under 35 U.S.C. §119 of Great Britain Patent Application No. 0902645.1, filed Feb. 17, 2009, the disclosures of which are expressly incorporated herein by reference.

FIELD OF THE INVENTION

This invention relates to devices for drug storage and drug administration to a patient.

BACKGROUND TO THE INVENTION

One type of drug delivery device known in the art is an injection apparatus which contains a medical, therapeutic, diagnostic, pharmaceutical or cosmetic compound (drug) before it is administered, and which is used to administer the compound through the skin of the patient via a hollow needle.

Injection apparatus of this type include pre-filled syringes and autoinjectors. These may contain a drug within a glass or plastic housing that is sealed at one end by a moveable rubber plunger, the internal surfaces of the housing and the plunger having been lubricated prior to being filled with drug by the application of silicone. The rubber plunger performs the dual functions of sealing an opening in the container prior to administration of the drug to the patient, and also of applying a force required to expel the drug from the container during administration of the drug to the patient.

Rubber plungers of this type typically incorporate multiple continuous sealing contact rings spaced apart from each other so that movement of the plunger within the container due to changes in atmospheric pressure during storage does not allow any surface of the container to be in contact at different times with both the drug and the unsterile environment outside the container. The multiple rings also increase the effective thickness of the rubber seal between the drug and the atmosphere outside the housing in order to provide a substantial barrier to gasses and moisture. A disadvantage of these multiple rings is that they increase the force required to move the plunger within the housing.

Other factors which affect the forces required to move the rubber plunger during administration of the drug to a patient can include the distribution and quantity of any silicone or other lubricant present on the surface of the housing or the plunger. In practice these forces can vary greatly due to variation in consistency of lubricant application during manufacture and to displacement of the lubricant and consequent bonding of the plunger to the housing over time. This has a corresponding impact on the design requirements and reliability of the drug delivery device. In addition any lubricants, such as silicone, in contact with the drug can have a detrimental effect on the drug, which can shorten the time for which the drug remains in a usable condition within the device.

Some prefilled syringes and autoinjectors incorporate a second opening within the housing through which the drug is expelled via a hollow hypodermic needle which is fixed to the housing. During storage of the filled device prior to administration of the drug, the needle is blocked by a rubber cap in order to seal the contents of the housing. This design has the disadvantage that it allows the drug to contact the inside of the needle and other materials such as the needle-retaining glue during storage. This design also requires the rubber cap to be removed before the drug is administered, requiring an additional separate action by the device user. This design also typically leaves a relatively large opening in the drug delivery device after the rubber cap has been removed and the drug administered, through which the contaminated needle can be accessed resulting in an increased risk of accidental transmission of blood-borne diseases due to needle stick injury.

SUMMARY OF THE INVENTION

The present invention is described in the attached appended claims.

The term "closure seal" as used herein in the claims and description means a seal which prevents deterioration or contamination of a drug in a container against foreseeable external factors in storage. A closure seal maintains the safety, identity, strength, quality, and/or purity of a drug in a container in compliance with official, regulatory or established requirements.

The present invention aims to address some or all of the problems described above by providing a drug delivery device or primary drug container with a plunger which typically requires lower forces to move it within the housing compared with a typical rubber plunger, and a separate sealing element to compensate for the reduced sealing performance of this plunger against gasses, moisture and biological contamination compared with a typical rubber plunger.

In one embodiment of the invention, neither the housing nor the plunger is lubricated with a separate lubricant for reducing frictional forces of the plunger during administration of the drug. The use of a low friction plunger that is not provided with a closure seal provides acceptably low and consistent forces during drug administration without this lubricant.

In one embodiment of the invention a low friction plunger is achieved through use of a substantially non-elastomeric material such as polypropylene, polyethylene or FEP (Fluorinated Ethylene Propylene) in a thin-wall seal design such as a 'cup' seal, where the seal between the plunger and the housing is augmented by the pressure of the medication on the seal during administration.

Preferably, the plunger is formed so that a component of the fluid pressure exerted by the drug during delivery of the drug is directed towards the sealing interface between the plunger and the housing. The fluid pressure exerted by the drug thereby augments the seal between the plunger and the housing. To achieve this, the plunger may be formed with a hollow portion in contact with the drug, such that the drug is in contact with and presses against an interior wall of the plunger. The advantage of this type of seal is that there is a strong correlation between the force that enables the seal (and hence creates friction that resists movement of the seal) and the force acting on the plunger to urge the drug out of the the hydraulic pressure of the drug reduces as drug exits the container into the patient, reducing the friction and allowing the plunger to move again, so a self-compensating mechanism is achieved. This type of seal is therefore less likely to 'stall' compared with conventional rubber syringe plungers. This type of plunger, which relies on pressure from the drug to form a seal, is not suitable for movement in a reverse direction, away from the drug, and so can be thought of as a "non-reversible" plunger. Movement in a reverse direction would likely allow air or any other gas, liquid or other contaminant on the other side of the seal to pass the seal and contaminate the drug and/or the patient.

Other designs of low friction plunger are also suitable for use in the present invention. For example, a design incorporating a two-component injection moulding of a TPE (thermoplastic elastomer) and a substantially non-elastomeric material, or incorporating an elastomeric O-ring in conjunction with a rigid plunger body, or incorporating an interference fit between the housing and a plunger made from a low-friction material such as polypropylene or polyethylene. The fact that these designs may provide only a single continuous sealing contact ring does not compromise the sterility and condition of the drug because of the use of the separate closure seal.

The plunger may incorporate other surfaces designed to contact with the housing in order to keep the plunger aligned axially within the housing during administration of the drug, in order to maintain the integrity of any seal between the plunger and the housing. The contact surfaces may be formed from a non-elastomeric material, and may have dimensions and/or form that prevent them from forming a substantive seal with the housing.

The separate sealing element of the closure seal is preferably formed from a material which is substantially impermeable to oxygen, moisture and biological contamination, and which can be pierced by a pusher to expel the drug. Such materials include 'trilaminate' foils. These foils may include an inner 'adhesive' layer, for example of polypropylene, which is appropriate for drug contact and which can be sealed to the housing heat or another method. They may also include a middle layer such as aluminium or a fluoropolymer to provide oxygen barrier performance. Alternative oxygen barriers include ethylene vinyl alcohol and polyamide. A further outer layer is generally used to provide strength, and may be made from paper, polyamide, PVC etc. Such materials also include foils which consist of a single material such as a fluoropolymer.

The sealing element is designed to be rupturable, i.e. under pressure it will break rather than peel or otherwise come away from the housing, and is typically thinner and less rigid than the housing.

The separate sealing element can be heat welded to the housing, or can be joined through other means such as ultrasonic, induction or laser welding, or through the use of separate adhesives, such as UV curable adhesives. Alternatively, the sealing element can be held in place by force alone, for instance by using a mechanical fastening component, preferentially in conjunction with a compression washer to maintain a sufficiently consistent force on the seal to accommodate manufacturing tolerances and dimensional changes of the components over time. This mechanical fastening component can typically be clipped or screwed into place, and would typically fasten to the housing.

In order to move the plunger to expel the drug during administration a pusher is positioned on the opposite side of the sealing element. This pusher can be moved to break the seal and move the plunger within the housing to dispense the drug. In one embodiment of the design this movement is caused by a user of the device applying a force to the device. In another embodiment this force comes from a stored power source such as a spring.

During manufacture, prior prefilled syringes and autoinjectors are almost always filled with drug through the same opening in the housing as the plunger is assembled. This process typically occurs in an aseptic environment. In a preferred aspect of the present invention, there are advantages in filling the drug through a second opening such as the opening through which the drug is expelled because this allows the plunger to be assembled, the sealing element attached, and then the system sterilised, all before the device enters the aseptic environment for filling with drug. However this requires that the second opening be sealed after filling.

One embodiment of the invention therefore incorporates a second sealing element which is designed to be appropriate for assembly within an aseptic environment. The second sealing element can be held in place by force alone, for instance by using a mechanical fastening component, preferentially in conjunction with a compression washer to maintain a sufficiently consistent force on the seal to accommodate manufacturing tolerances and dimensional changes of the components over time. This mechanical fastening component can be clipped or screwed into place, and would typically fasten to the housing. Alternatively, the second sealing element can be heat welded to the housing, or can be joined through other means such as ultrasonic, induction or laser welding, or through the use of separate adhesives such as UV curing adhesives.

A further aspect of the invention incorporates a mechanism to rupture the second sealing element and allow the drug to pass through a hollow hypodermic needle during administration of the drug to a patient. This approach prevents the drug from contacting the needle or other associated materials during storage of the device, and avoids the use of a large needle-blocking rubber cap which requires a separate removal action by the user before the drug is administered, and which can cause the used needle to be exposed after administration.

In a still further aspect of the invention, a primary drug container may comprise: a housing containing a drug to be dispensed, the housing having a first end defining an opening; a plunger, positioned within the housing, in contact with the drug; and a first sealing element providing a first closure seal across the first opening of the housing; wherein the plunger does not form a closure seal with the housing and includes a hollow portion such that, in use, the drug is in contact with and presses against an interior wall of the hollow portion. With this type of plunger, in use, the fluid pressure exerted by the drug augments or substantially creates the seal between the plunger and the housing, but the plunger provides a predictable, low friction contact with the housing. This type of plunger can be described as forming a self energising seal, and an example is a cup seal plunger. The plunger does not suffer from sticking and lubricant may not be required. This type of primary drug container is particularly suitable for automated drug delivery mechanisms, requiring movement of the plunger in only a single direction. Because the plunger relies on pressure from the drug to form a seal, it is not suitable for movement in a reverse direction, away from the drug, and so can be thought of as a "non-reversible" plunger. Movement in a reverse direction would likely allow air or any other gas, liquid or other contaminant on the other side of the seal to pass the seal and contaminate the drug and/or the patient.

In this aspect, the closure seal is preferably designed to be piercable, but may be peelable or removed in other ways during use. It should be apparent that other features of this aspect of the invention, such as the choice of materials for the housing, closure seal and plunger, and the means of fastening the closure seal to the housing can be the same as described with reference to the embodiments described above.

Although the present invention is primarily described herein in relation to needle based devices, such as autoinjectors and syringes, i.e. devices including a hollow hypodermic needle through which the drug is delivered to the patient, the invention is equally applicable to non-needle based drug delivery devices. The phrase "non-needle based" as used herein refers to drug delivery devices that do not include a hypodermic needle through which the drug is delivered in use. Drug delivery devices that may comprise a primary drug container in accordance with the invention include inhalers, insufflators, droppers, tubes, bottles, vials, applicators and other dispensers of drugs including drugs in the form of liquids, creams, gels, powders, tablets, granules, gasses, aerosols, sprays and suspensions for parenteral (including intradermal, subcutaneous, intramuscular and intravenous), topical, nasal, oral, aural, sublingual, rectal, vaginal and other applications. The invention may be used in devices that require manual force to dispense the drug as well as with a variety of automated dispensing mechanisms.

BRIEF DESCRIPTION OF THE DRAWINGS

Examples of the present invention will now be described in detail with reference to accompanying drawings, in which:

FIG. 10 is a section view of another example of the invention with a first sealing element retained by a mechanical fastening which is retained by clips to the housing;

FIG. 11 is an exploded view of the housing, first sealing element, compression washer and mechanical fastening of FIG. 10;

FIG. 12 is a view of the primary container of another example of the invention before filling, showing a separate housing subassembly and a separate second sealing subassembly;

FIG. 13 is a section view of the primary container of another example of the invention before filling, showing a separate housing subassembly and a separate second sealing subassembly;

FIGS. 14a, 14b, 14c and 14d are section views of the filling sequence of the primary container of FIG. 12;

DETAILED DESCRIPTION

For the purposes of describing the invention the primary drug container is defined as the housing, plunger, and any sealing components required in order to contain the drug within the housing.

Figure 1:
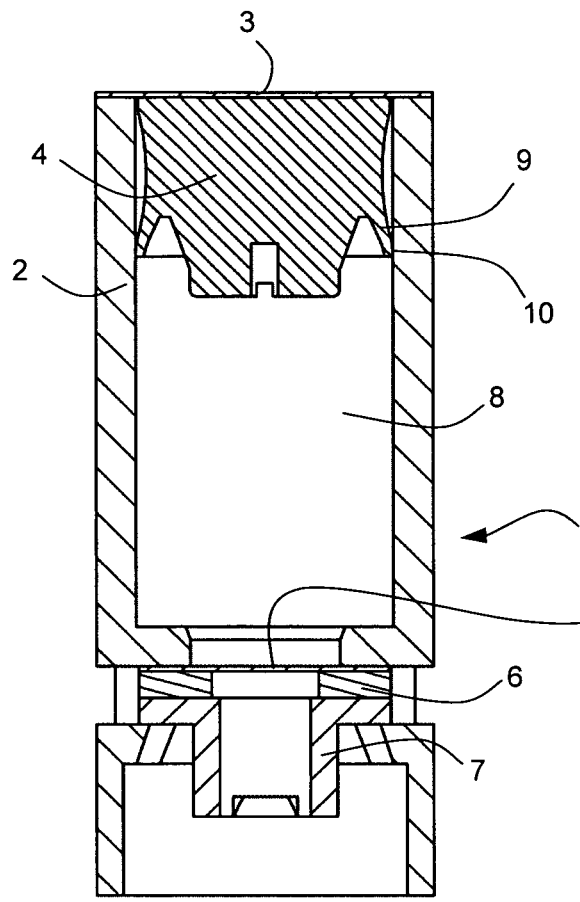
FIG. 1 is a longitudinal cross-section of an example of a primary drug container.

FIG. 1 shows one example of a primary drug container 1 for use in a drug delivery device in accordance with the present invention. The primary drug container 1 comprises a housing 2, a first sealing element 3, a plunger 4, a second sealing element 5, a compression washer 6 and a mechanical fastening component 7. The housing 2, the first sealing element 3 and the second sealing element 5 form a sealed container which is substantially impermeable to moisture, atmospheric gasses including oxygen, and biological contamination. A drug 8 is contained within the container prior to administration to a patient. The primary drug container can form part of a drug delivery device, but can be filled and sealed in a separate environment from assembly to the rest of the drug delivery device, in order to protect the drug from contamination. The plunger 4 includes a sealing feature 9 with a sealing lip 10 in contact with the housing 2. The plunger 4 is positioned close to the first sealing element 3 and is designed to minimise the volume of drug which can reside between the sealing lip 10 and the first sealing element 3. During administration of the drug 8 the pressure of the drug fluid acts on the sealing feature 9 to increase the sealing force between the sealing lip 10 and the housing 2. The first sealing element 3 is welded to the housing 2. The second sealing element 5 is maintained in position against the housing 2 by the mechanical fastening component 7 acting on it through the compression washer 6.

The housing 2 in this embodiment may be formed from plastic or glass. The first sealing element in this embodiment is formed from a trilaminate foil including an inner 'adhesive' layer, for example of polypropylene, which is appropriate for drug contact and which can be sealed to the housing heat or another method, a middle layer such as aluminium or a fluoropolymer to provide oxygen barrier performance and an further outer layer to provide strength, which may be made from paper, polyamide, or PVC.

The plunger in this embodiment is formed from a substantially non-elastomeric material such as polypropylene, polyethylene or FEP (Fluorinated Ethylene Propylene) in a thin-wall 'cup' seal, where the seal between the plunger and the housing is augmented by the pressure of the medication on the seal during administration.

Figure 2:
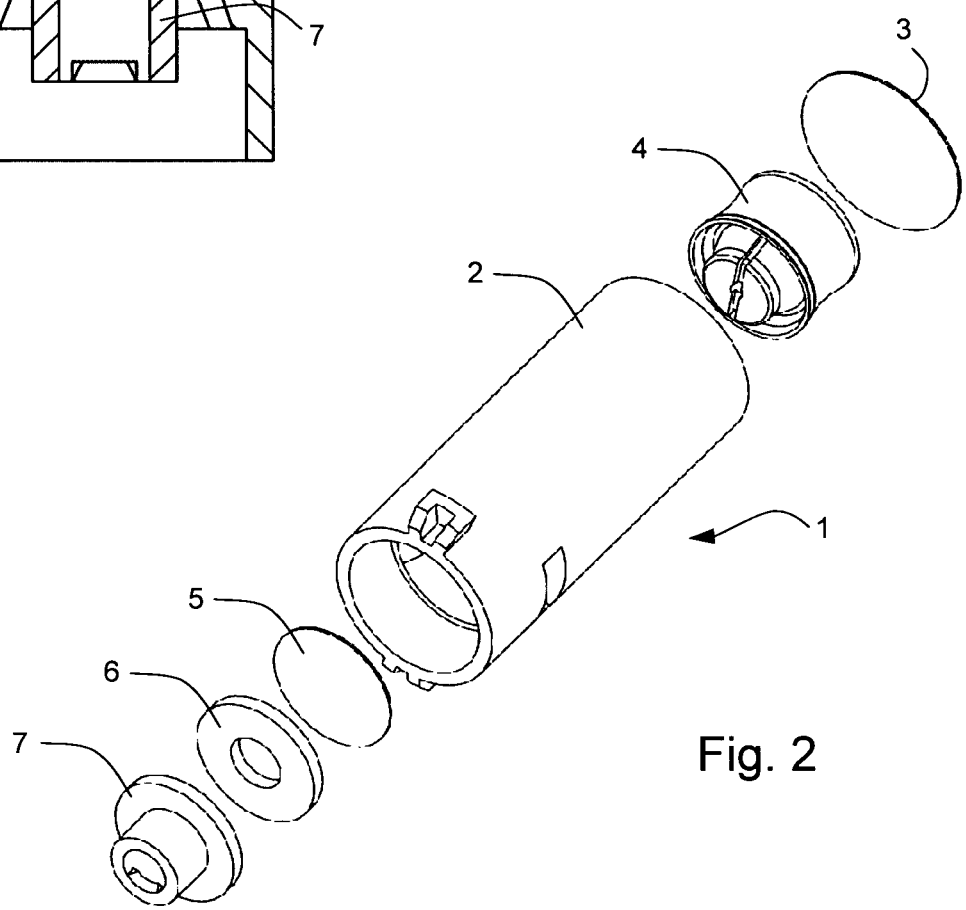
FIG. 2 is an exploded view of the primary drug container from FIG. 1.

FIG. 2 shows an exploded view of the primary drug container 1 of FIG. 1 without the drug 8.

Figure 3:
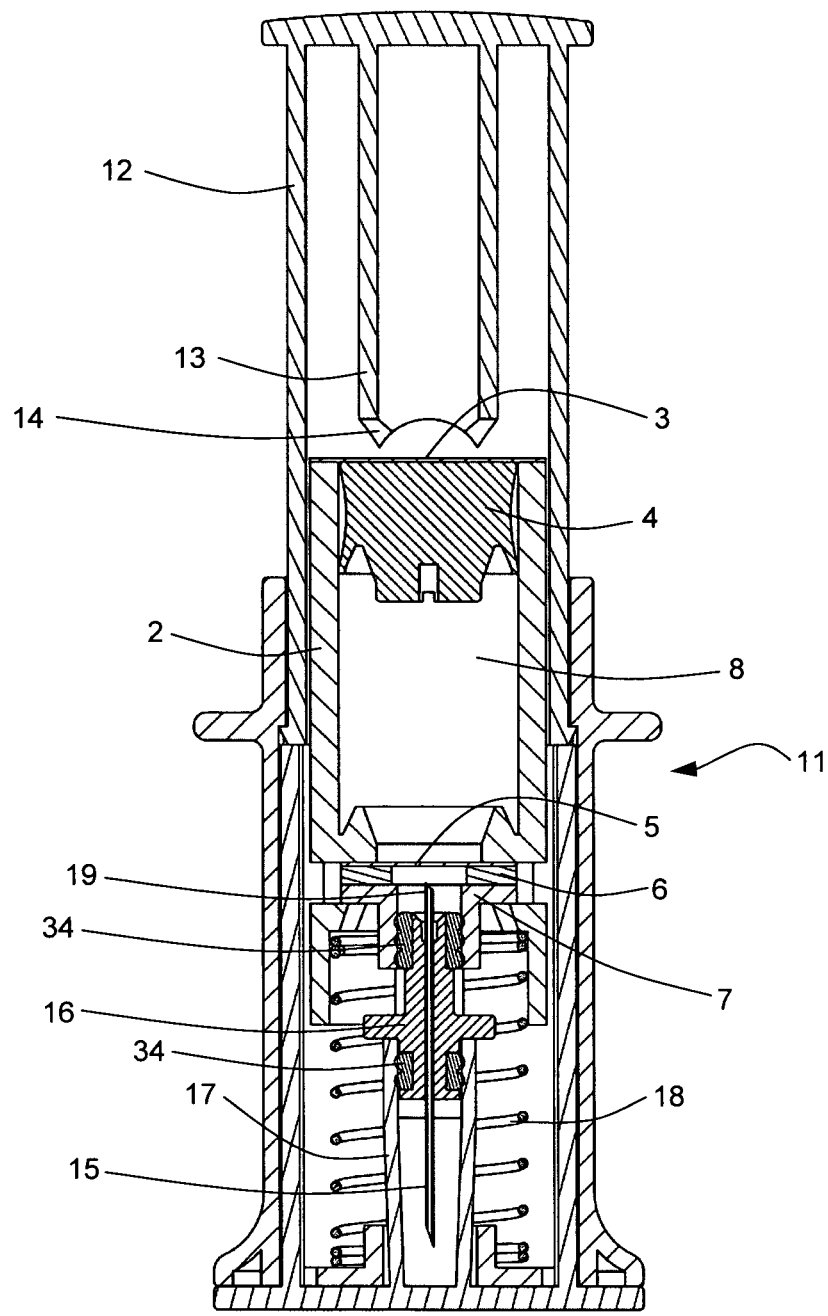
FIG. 3 is a longitudinal cross-section through an example of a drug delivery device incorporating the present invention before administration of the drug to the patient.

FIG. 3 shows an example of a drug delivery device 11 in accordance with the present invention in its stored state before the drug 8 is administered to a patient. The drug delivery device 11 includes the primary drug container 1 of FIG. 1. It also includes a plunger rod 12 which incorporates a pusher 13 with a piercing feature 14. During administration of the drug to a patient, the piercing feature 14 pierces the sealing element 3 and urges the plunger axially along the housing 2 to expel the drug 8 due to the application of force to the plunger rod 12 by the person administering the drug.

Application of force to the plunger rod 12 by the person administering the drug also causes a hollow hypodermic needle 15 to extend through the patient's skin, and the opposite end of the needle to pierce the second sealing element 5 allowing the drug 8 to flow through the needle 15 and into the patient. The needle 15 is mounted in a needle hub 16 which is sealed by a needle hub seal 34 to prevent leakage of the drug 8 during administration. The needle hub seal 34 further seals to a removable needle shield 17 which keeps the needle 15 sterile and protects it from damage prior to administration of the drug 8. A spring 18 urges the end of the needle 15 out of the patient back into the device when the person administering the drug 8 releases the force that they are applying to the plunger rod 12.

Figure 4:
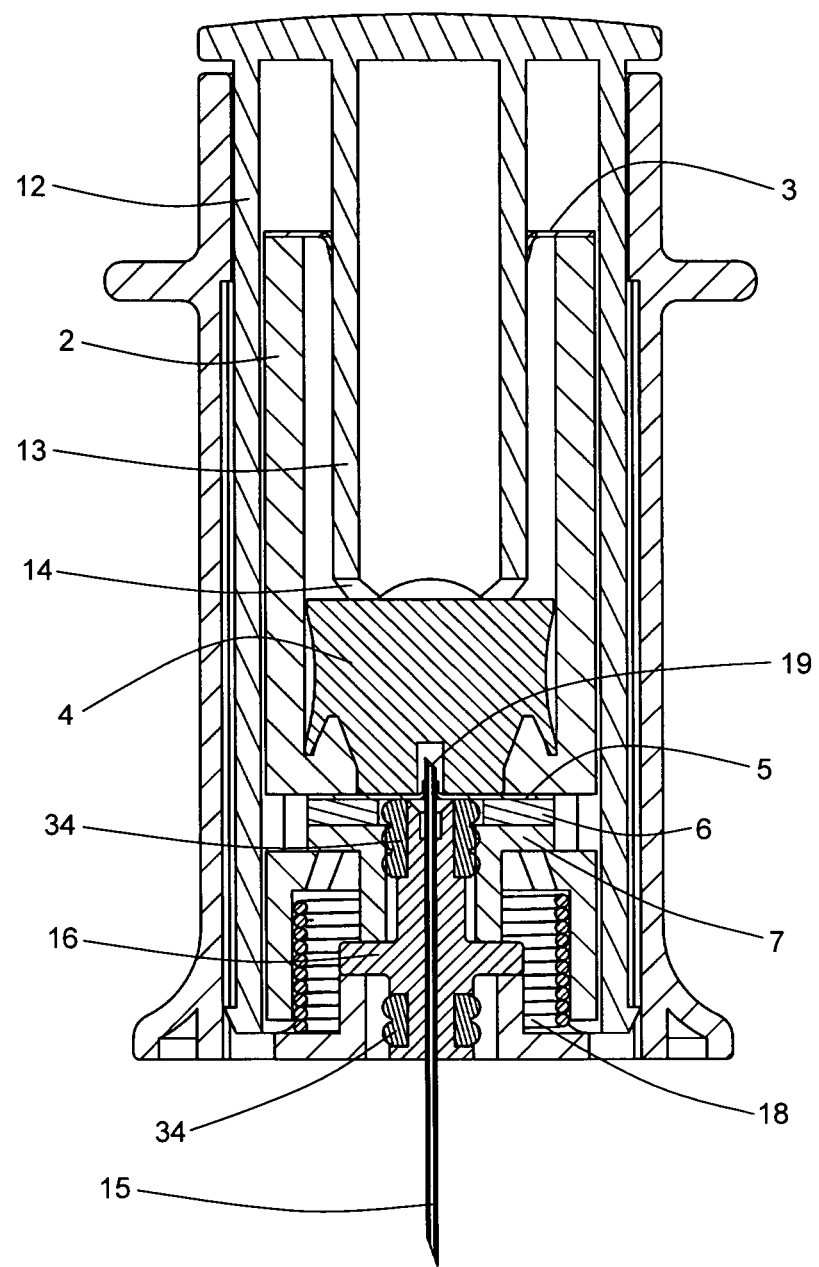
FIG. 4 is the invention in FIG. 3 after administration of the drug to the patient.

FIG. 4 shows the drug delivery device of FIG. 3 in its used state after the drug 8 has been delivered but before the needle 15 has been withdrawn from the patient. The pusher 13 has forced the housing 2 forwards, which in turn has caused the end of the needle 15 to be extended forwards into the patient and the other end of the needle 19 to pierce the second sealing element 5. The pusher 13 has pierced the first sealing element 3 and urged the plunger 4 forwards to expel the drug 8.

Figure 5:
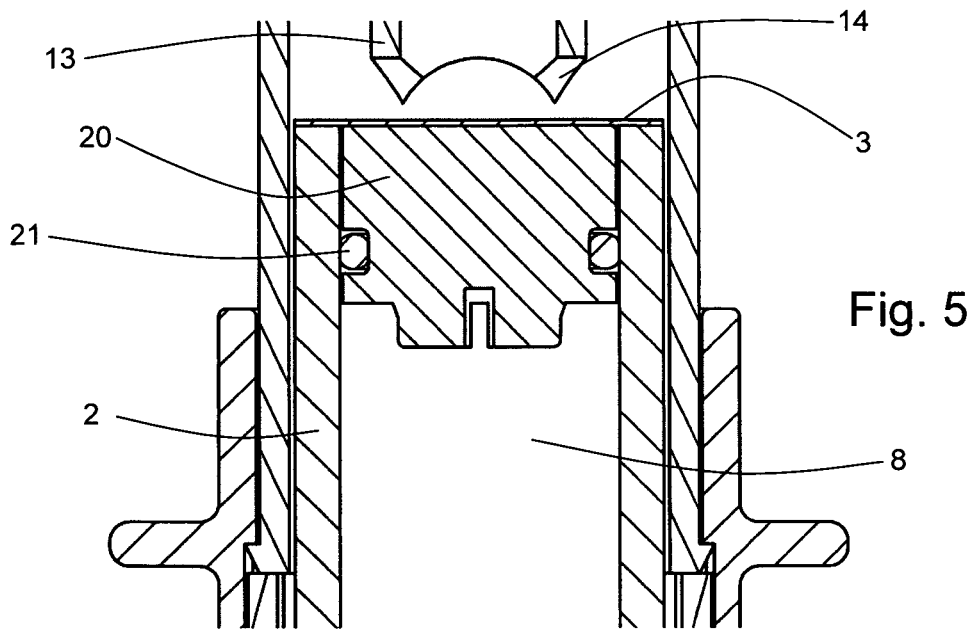
FIG. 5 is a detail view of FIG. 3 showing an alternative plunger design which includes an O-ring.

FIG. 5 shows a detail view of the design of FIG. 1 incorporating an alternative design of plunger 20 which is made from a substantially rigid material and which includes an elastomeric O-ring 21.

Figure 6:
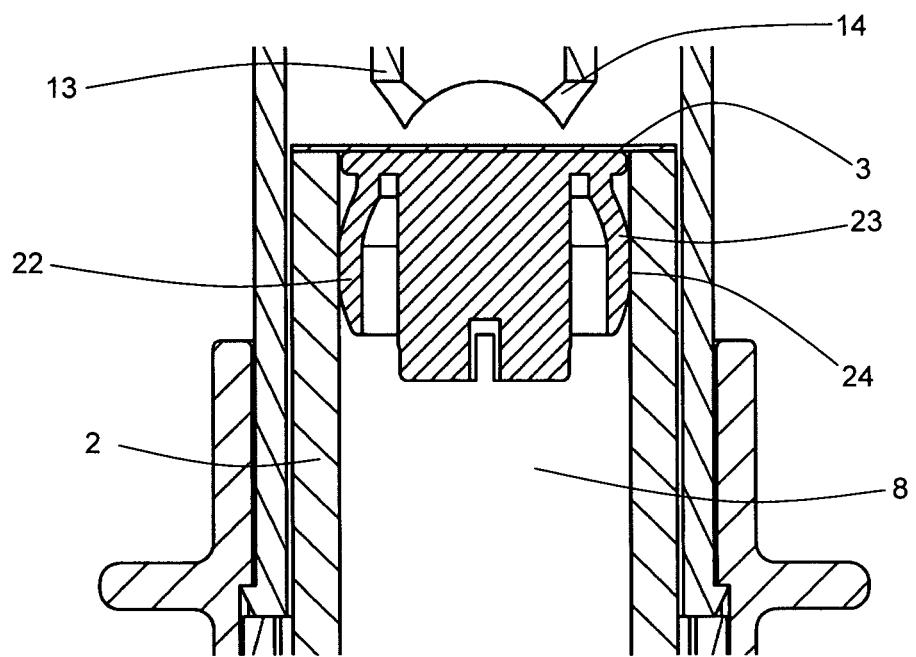
FIG. 6 is a detail view of FIG. 3 showing an alternative plunger design which includes an interference seal.

FIG. 6 shows a detail view of the design of FIG. 1 incorporating an alternative design of plunger 22 which includes a stronger sealing feature 23 compared with the first plunger 4 described above. The plunger 22 differs from the plunger 4 described above in that the seal relies more on an interference fit between the housing 2 and the sealing feature 23. However, this seal still provides low friction with the housing and is not sufficient to provide a closure seal to maintain the condition of drug.

Figure 7:
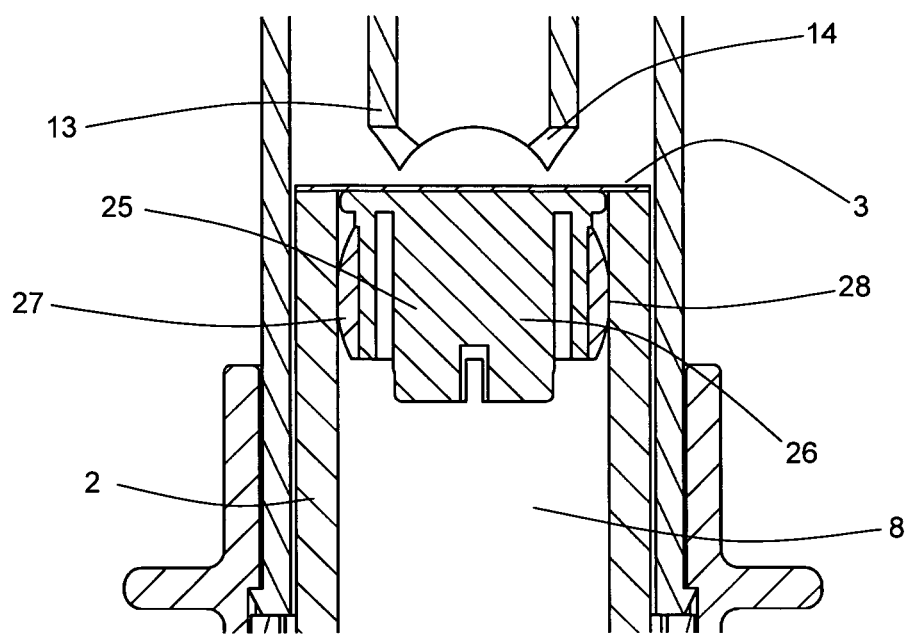
FIG. 7 is a detail view of FIG. 3 showing an alternative plunger design which is comprised of a two-component injection moulding of a TPE (thermoplastic elastomer) and a substantially non-elastomeric material.

FIG. 7 shows a detail view of the design of FIG. 1 incorporating an alternative design of plunger 25 which includes both a substantially rigid material such as polypropylene or polyethylene and a second elastomeric material such as TPE (thermoplastic elastomer). The rigid part of the plunger 26 supports the elastomeric part 27 to form a seal at the sealing contact area 28 with the housing 2. In one embodiment of this design the plunger is manufactured using a 'two-shot' injection moulding process involving two separate materials within a single mould tool, or by otherwise over-moulding the elastomeric part 27 onto the substantially rigid part 26. Again the seal formed between the plunger and the contact area 28 is not sufficient to provide a closure seal sufficient to maintain the drug in a useable condition for its shelf-life. Closure seal 3 is provided for that purpose.

Figure 8:
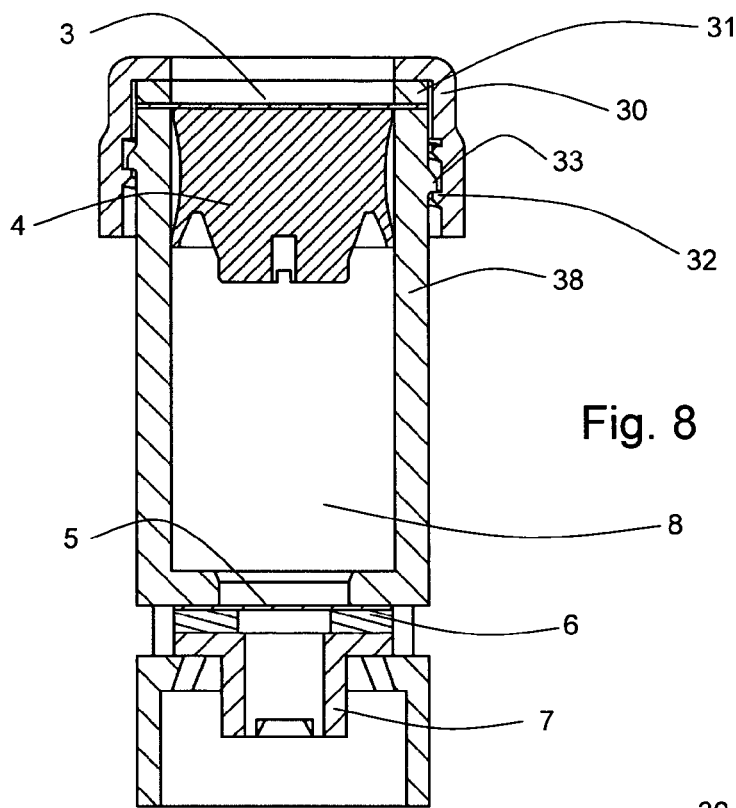
FIG. 8 is a section view of another example of the invention with a first sealing element retained by a mechanical fastening which is retained by a screw thread.

FIG. 8 is a section view of another example of a primary container identical to FIG. 1 other than that the first sealing element 3 is retained by a mechanical fastening component 30 in conjunction with a compression washer 31. The compression washer maintains a sufficiently consistent force on the first sealing element to accommodate manufacturing tolerances and dimensional changes of the components over time. This mechanical fastening component 30 is retained by a screw-thread 32, and is screwed to a corresponding thread detail 33 on the housing 38 during the assembly process. This assembly process can take place either before or after filling of the drug 8 into the primary container.

Figure 9:
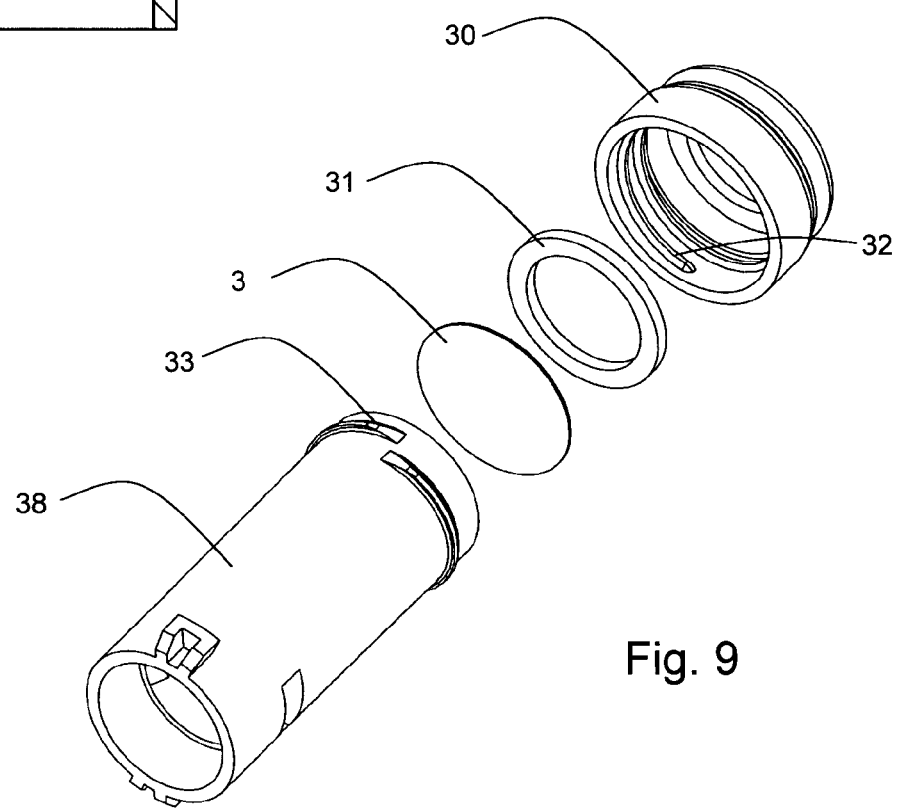
FIG. 9 is an exploded view of the housing, first sealing element, compression washer and mechanical fastening of FIG. 8.

FIG. 9 is an exploded view of the housing 38, first sealing element 3, compression washer 31 and mechanical fastening component 30 of FIG. 8

FIG. 10 is a section view of another example of a primary container identical to FIG. 8 except that the mechanical fastening component 35 is retained by fastening surfaces 36 which engage with latch details 37 on the housing 39. This allows the first mechanical fastening component 35 to be assembled directly to the primary container 39 as a 'push-fit' which does not require a screwing action.

FIG. 11 is an exploded view of the housing 39, first sealing element 3, compression washer 31 and mechanical fastening component 35 of FIG. 10.

FIG. 12*a* and FIG. 12*b* together show an example of partially assembled primary drug container which is capable of being filled and then assembled together. The primary drug container comprises a container portion 52 and a lid portion 53. The primary drug container is identical to the primary drug container of FIG. 1 and FIG. 3 with the addition of a needle mechanism similar to that shown in FIG. 3. In this example of the invention the two subassemblies of FIG. 12*a* and FIG. 12*b* as described are supplied to the filling process, where drug is filled through an opening 40 in the container portion 52 and then the lid portion 53 is assembled to the container portion 52 to seal the primary drug container.

FIG. 13*a* and FIG. 13*b* show the corresponding section views of the container portion 52 and lid portion 53 of FIG. 12*a* and FIG. 12*b*

FIGS. 14*a* to 14*d* show the filling sequence for FIG. 12. FIG. 14*a* shows the container portion 52 ready for filling. The container with the first closure seal 3 and the plunger 4 can be assembled outside the aseptic environment. The container assembly is then sterilised before being filled with drug in an aseptic environment. FIG. 14*b* shows the container portion 52 after it has been filled with drug. FIG. 14*c* shows the lid portion 53 in position above the container portion 52 ready for assembly. Again, the entire lid assembly can advantageously be assembled outside the aseptic environment and then sterilised before being united with the container assembly in an aseptic environment. FIG. 14*d* shows the lid portion 53 and the container portion 52 assembled together with the drug.

Figure 15:
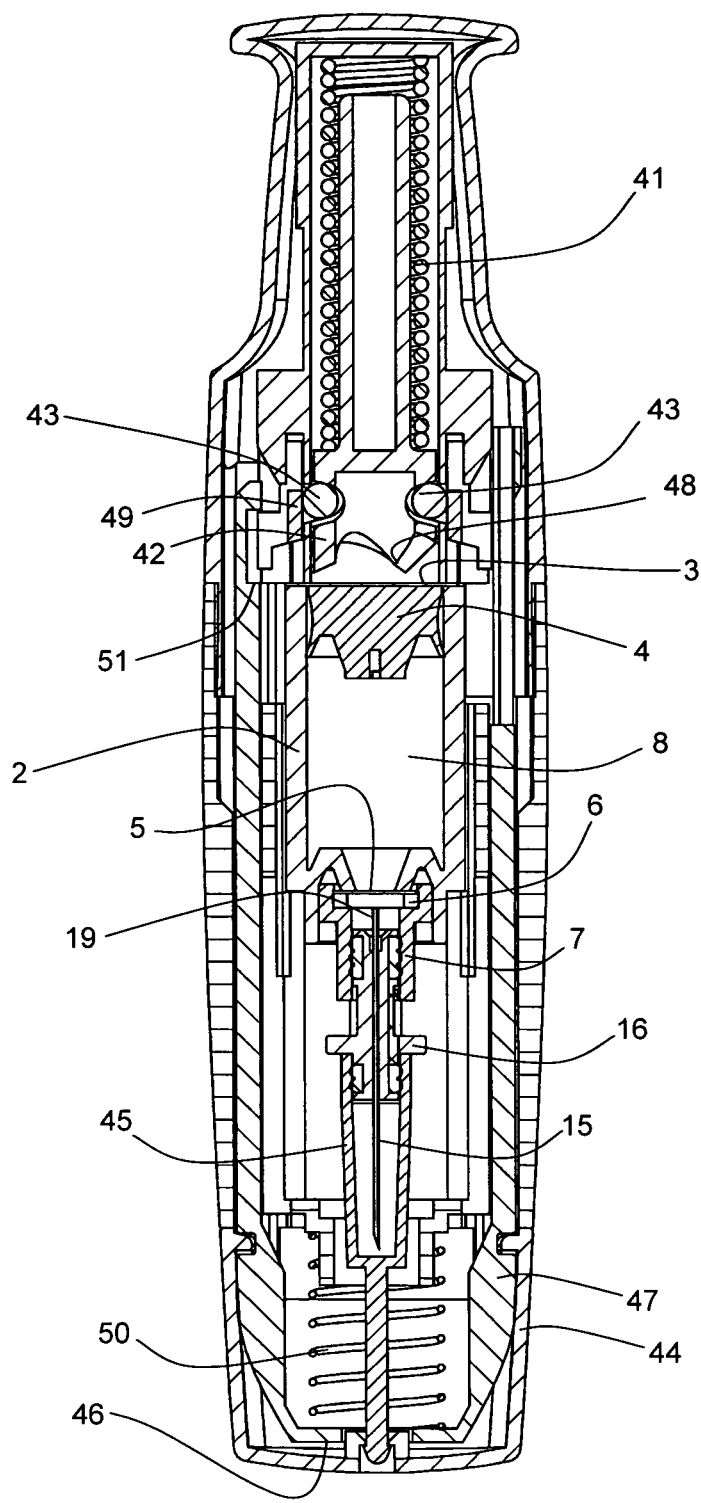
FIG. 15 is a section view of an example of an auto-injector incorporating the present invention before administration of the drug to the patient.

FIG. 15 shows a section view through another example of the invention where the drug delivery device is an auto-injector. The primary drug container is significantly similar to the primary drug container of FIG. 1, and to both the primary container and needle mechanism of FIG. 3, both described in detail above. A main drive spring 41 applies a force to a pusher 42, which is retained by two locking rollers 43. In order to administer the drug an auto-injector user removes the cap 44 with the attached needle shield 45 and presses the exposed front surface 46 of the needle cover 47 onto the patient injection site, pushing the needle cover 47 back into the auto-injector. This allows the locking rollers 43 to move out of the way of the pusher 42, so that the spring 41 can move the pusher 42 forwards. This in turn causes the piercing elements 48 of the pusher to pierce the first sealing element 3 and move the primary drug container axially through the auto-injector, which in turn moves the needle 15 forwards into the patient. This axial movement of the primary drug container also causes the other end of the needle 19 furthest from the patient to pierce a second sealing element 5, allowing the plunger 4 to move axially through the housing 2 and the drug 8 to be administered through a hollow hypodermic needle 15 into a patient.

Figure 16:
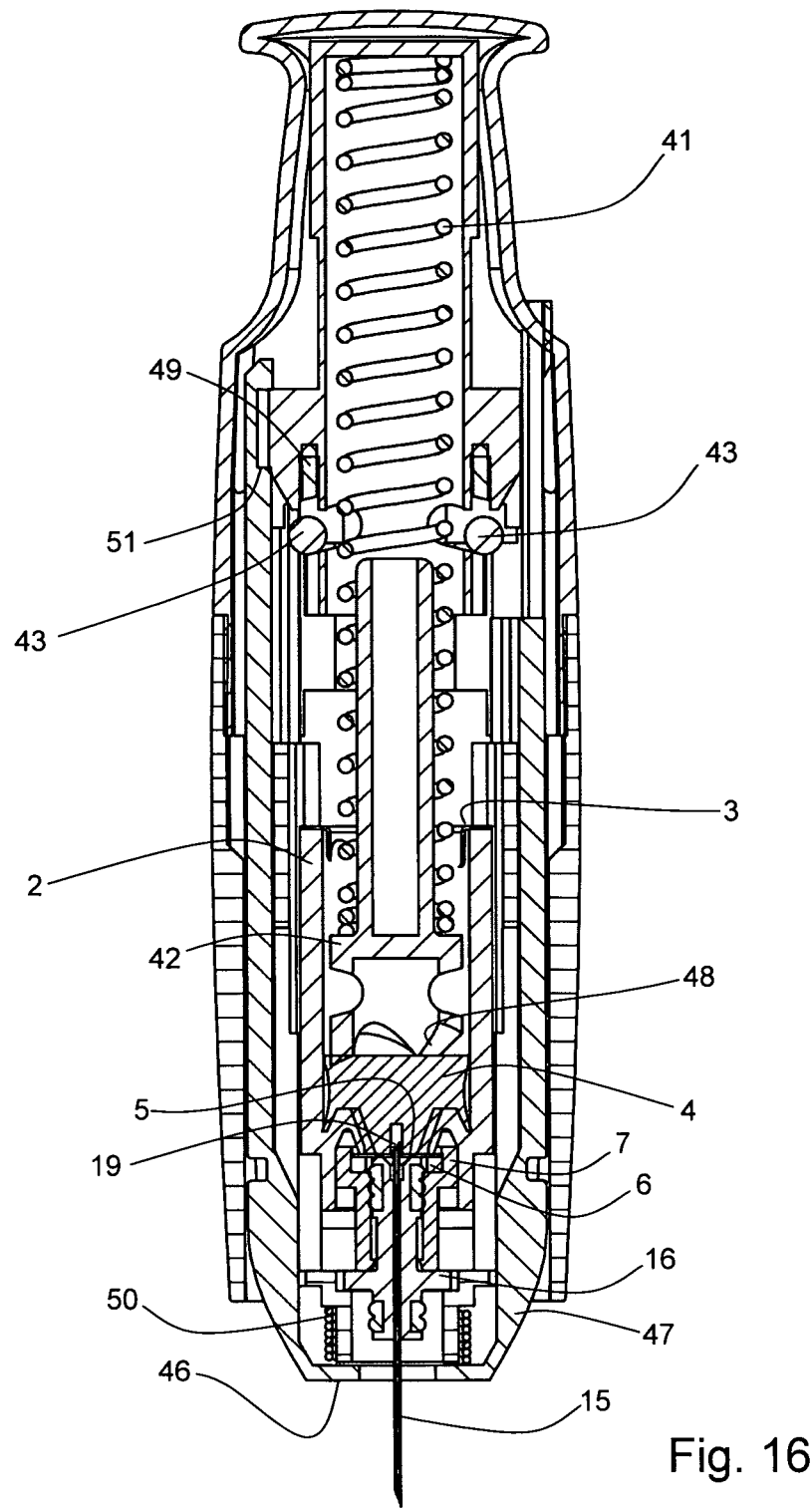
FIG. 16 is a section view of the auto-injector of FIG. 15 immediately after administration of the drug to the patient.

FIG. 16 shows FIG. 15 immediately after administration of the drug to the patient. The needle 15 is extended into the patient. The other end of the needle 19 furthest from the patient has pierced the second sealing element 5 and the plunger 4 has been urged axially through the housing 2 by the pusher 42. The first sealing element 3 has been broken by the pusher piercing elements 48.

Figure 17:
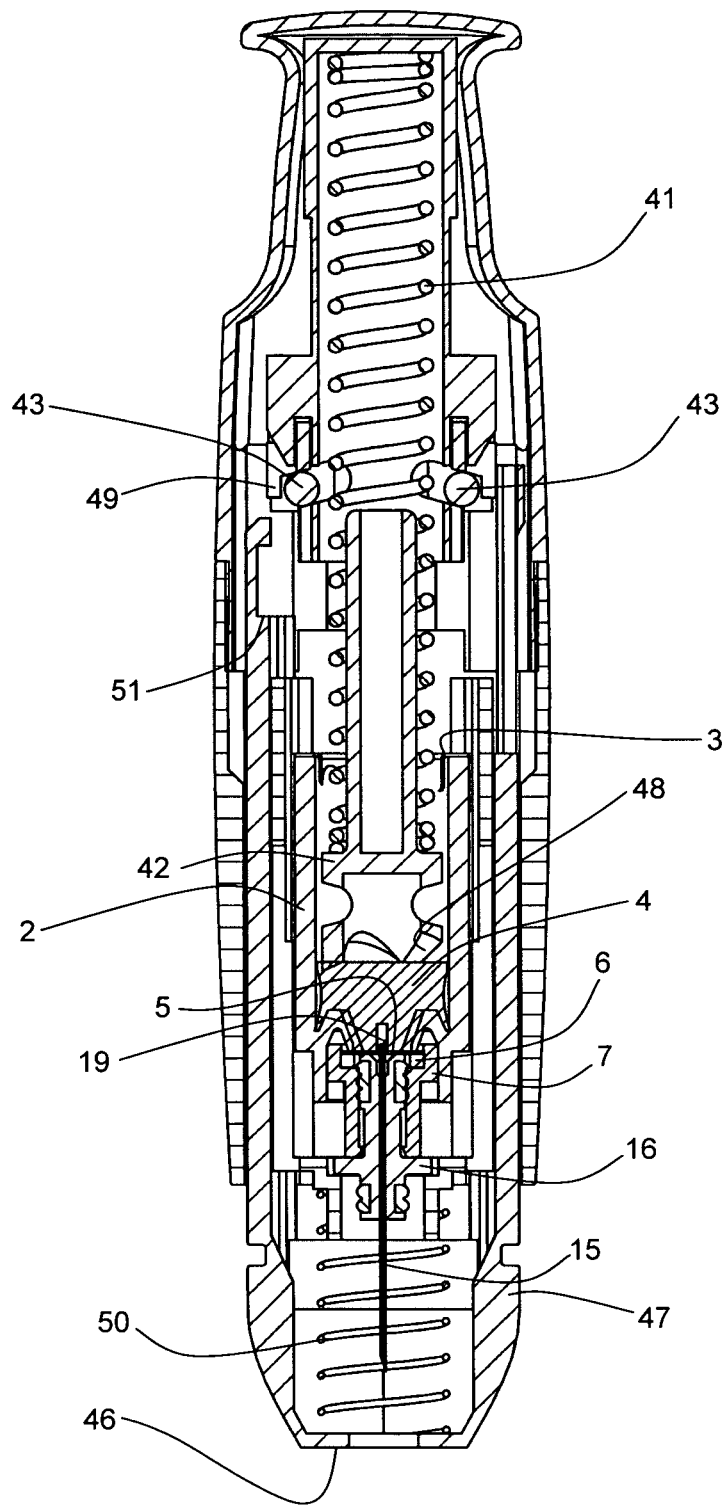
FIG. 17 is a section view of the auto-injector of FIG. 15 after the user has removed the auto-injector from the patient and a needle safety mechanism has deployed.

FIG. 17 shows FIG. 15 after the user has stopped applying the auto-injector to the skin of the patient and the needle cover spring 50 has forced the needle cover 47 to extend so that it shields the used needle 15 to reduce the risk of accidental transmission of blood-borne diseases due to needle stick injury. Locking details 51 at the back of the needle cover 47 prevent the needle cover 47 from moving back into the auto-injector.

Figure 18:
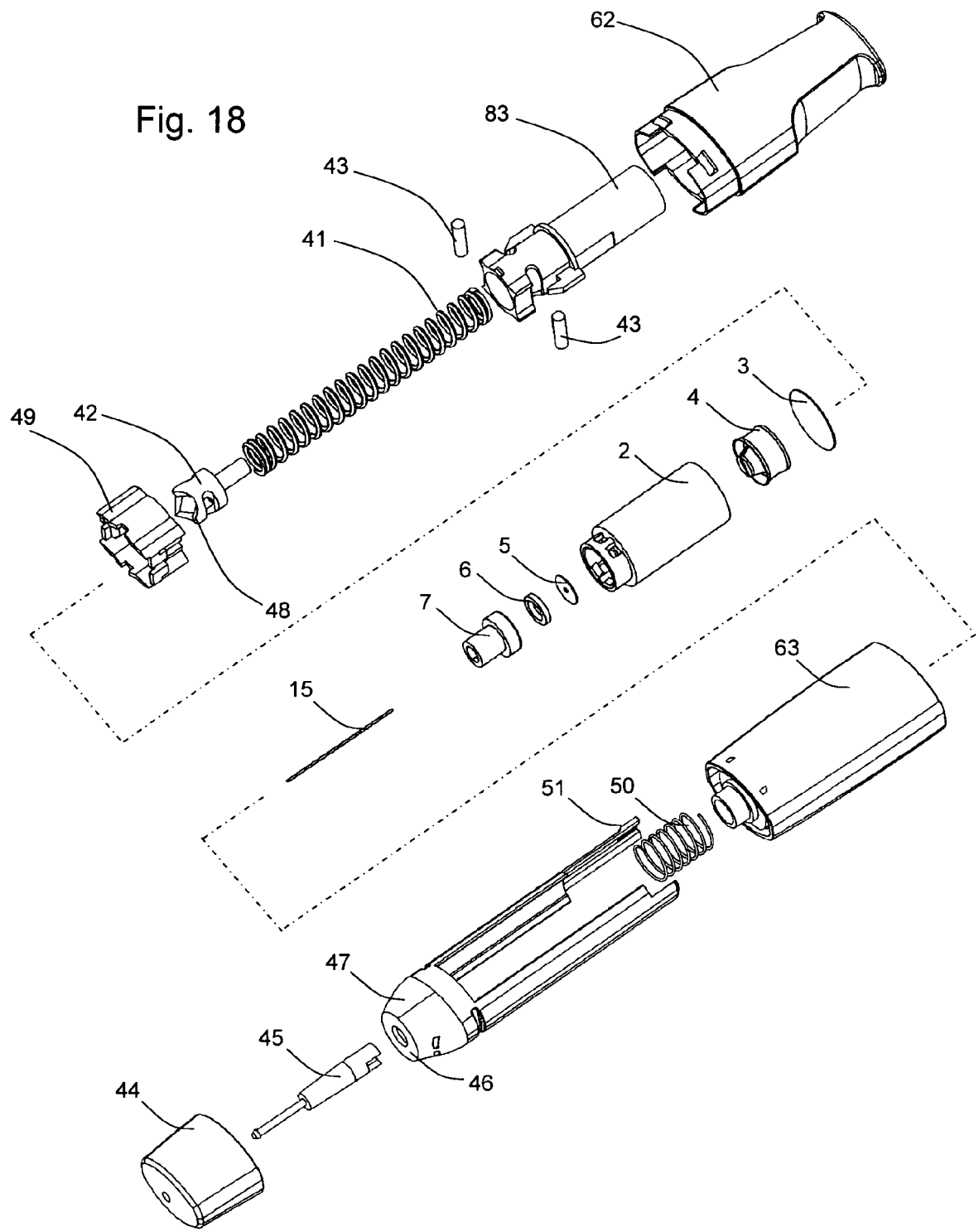
FIG. 18 is an exploded view of the auto-injector of FIG. 15.

FIG. 18 is an exploded view of FIG. 15 showing the components of the auto-injector. A rear cover 62, a front cover 63 and a cap 44 form the outer casing of the auto-injector. An inner housing 83 supports the spring 41.

Figure 19:
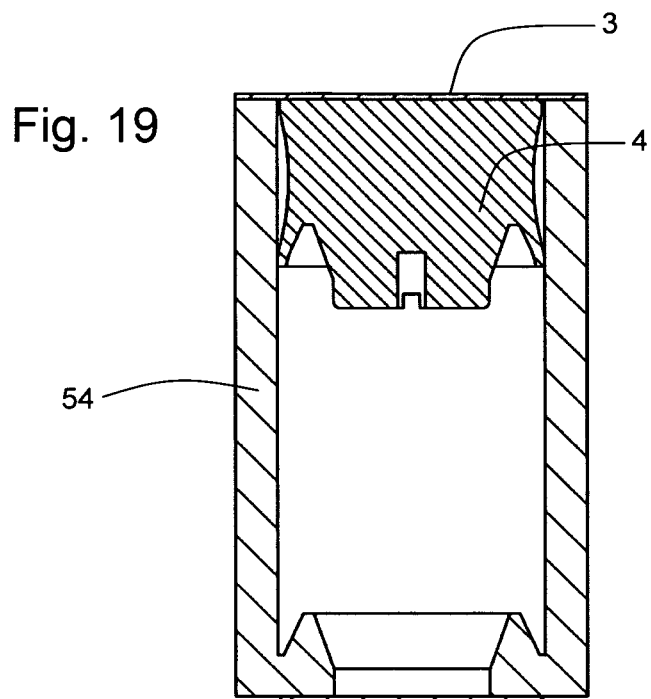
FIG. 19 is a section view of FIG. 3 showing an alternative design of the second sealing element welded to the housing.

FIG. 19 shows a section view of FIG. 1 incorporating an alternative design of housing 54 and second sealing element 55 where the second sealing element 55 is welded or attached with adhesive to the housing, and therefore does not require the compression washer 6 or mechanical fastening component 7 shown in FIG. 1.

Figure 20:
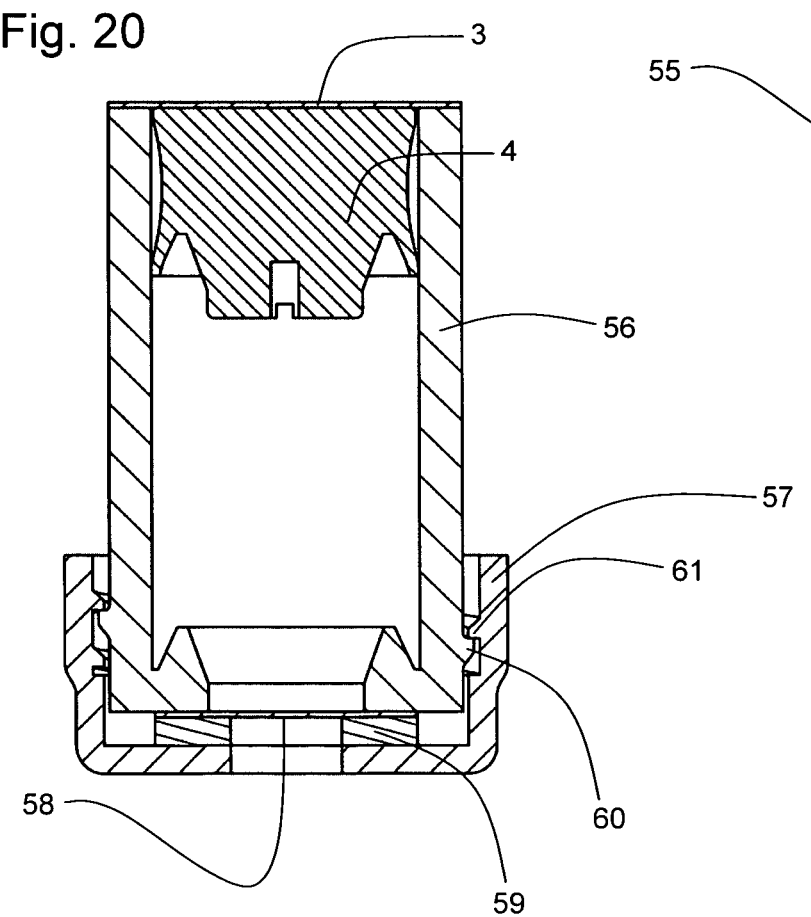
FIG. 20 is a section view of FIG. 3 showing an alternative design with a second sealing element retained by a mechanical fastening which is retained by a screw thread.

FIG. 20 shows a section view of FIG. 1 incorporating an alternative design of housing 56 and second sealing element 58 where the second sealing element 58 is attached by a mechanical fastening component 57 and compression washer 59 where the mechanical fastening component 57 is retained preferentially to the housing 56 by a screw thread 61 which engages in a corresponding thread detail 60 on the housing.

Figure 21:
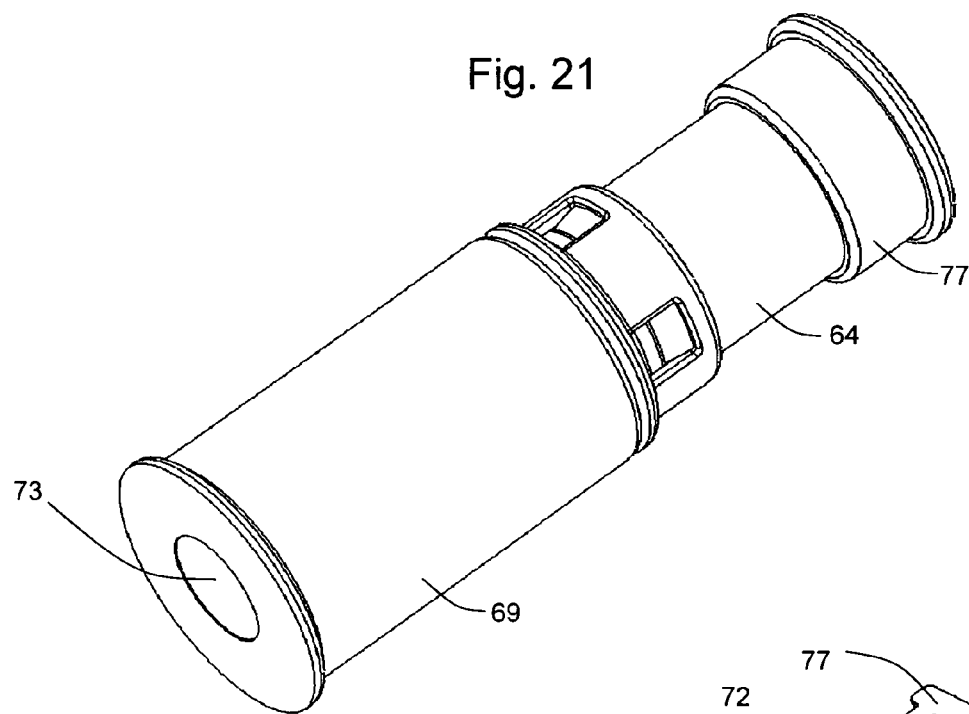
FIG. 21 is a view of an alternative embodiment of the invention in which the drug is filled into the housing through the same opening in the housing through which the plunger is assembled.

FIG. 21 shows another embodiment of the invention where the opening in a housing through which the drug is filled is the same as that used to assemble the plunger.

Figure 22:
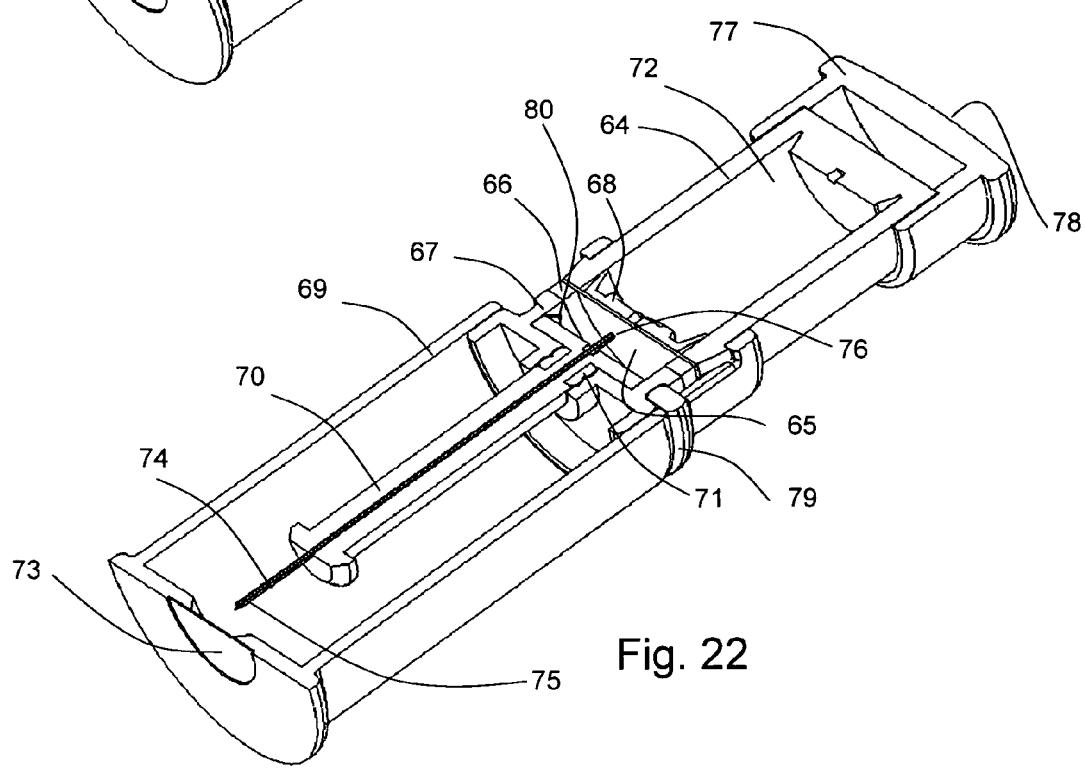
FIG. 22 is a three-dimensional section view of FIG. 21.

FIG. 22 is a three-dimensional section view of FIG. 21 showing the components in more detail. A housing 64 is sealed by a first sealing element 65 which is retained by a compression washer 66 and mechanical fastening component 67. Inside the housing 64 a plunger 68 is positioned adjacent to the first sealing element 65, and may be attached to the sealing element 65 through a weld or adhesive. A lower body 69 is axially moveable in relation to the housing 64, and contains a needle hub 70 which in turn is axially moveable in relation to the lower body 69. A seal 71 incorporated into the needle hub 70 prevents accidental movement of the needle hub 70 before administration of the drug 72. Piercing teeth 80 on the needle hub 70 pierce the first sealing element 65 during administration of the drug, allowing the needle hub 70 to move a portion of the first sealing element 65 including the part joined to the plunger 68 and also the plunger 68 itself axially through the housing 64. A second sealing element 73 maintains the cleanliness and sterility of a needle 74 before administration of the drug 72, and is pierced by the needle 74 during administration of the drug 72. The needle 74 is fixed into the needle hub 70 so that the end of the needle 75 nearest the second sealing element 73 can enter the patient during drug administration, and so that the other end of the needle 76 furthest from the patient can pierce the first sealing element 65 during drug administration to allow the drug 72 to flow through the needle 74. A button component 77 provides a suitable surface 78 for the person administering the drug to apply a force to in order to facilitate drug administration. A locking ring 79 prevents accidental activation of the device, and is removed prior to administration of the drug 72.

Figures 23, 24:
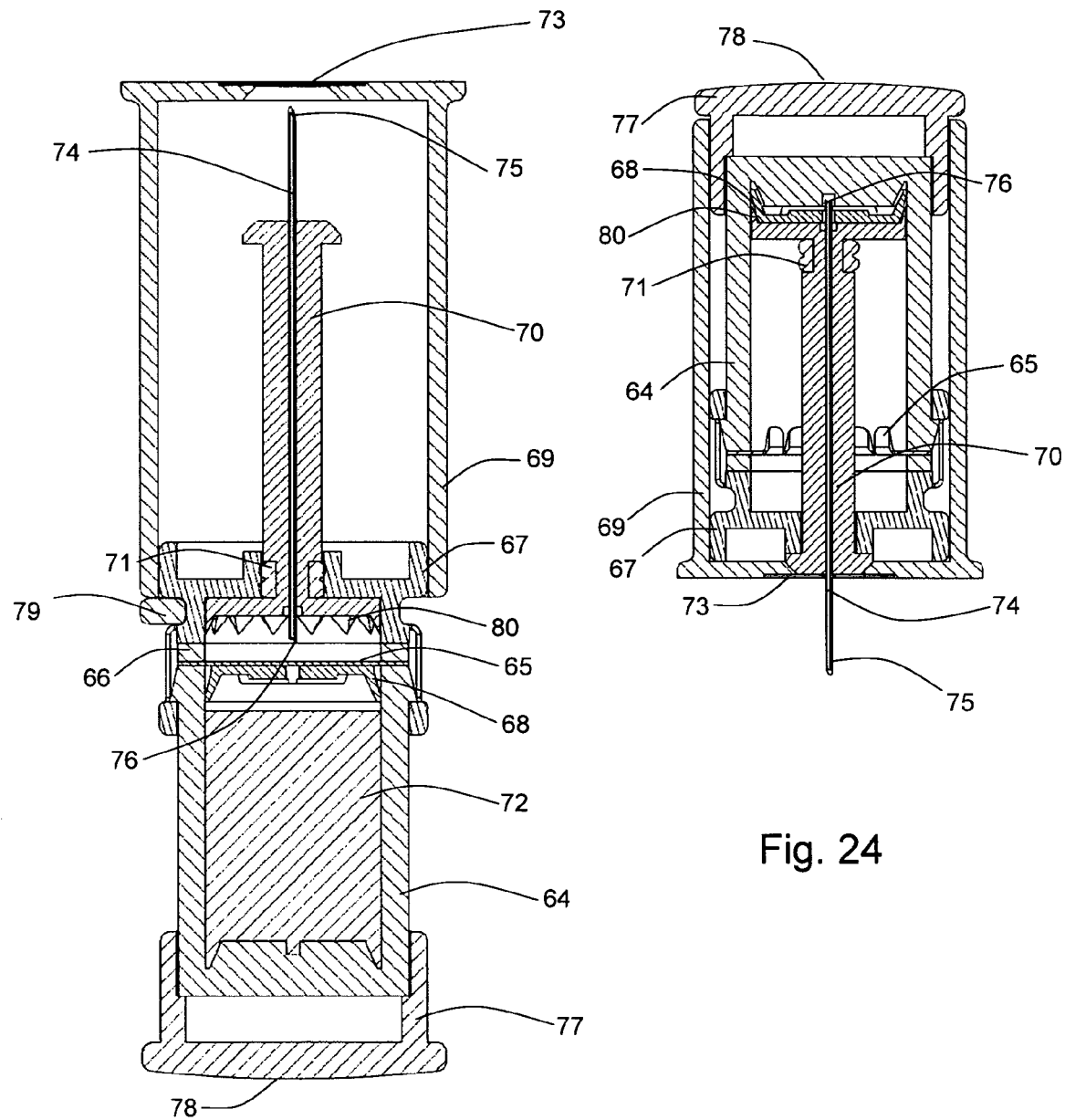
FIG. 23 is a section view of FIG. 21 before administration of the drug to a patient.
FIG. 24 is a section view of FIG. 21 after administration of the drug to a patient.

FIG. 23 shows a section view of FIG. 21 before administration of the drug 72.

FIG. 24 shows a section view of FIG. 21 after administration of the drug 72, and illustrates the first sealing element 65 after it has been pierced by the needle hub 70, the second sealing element 73 after it has been pierced by the needle 74, and the plunger 68 after it has been urged axially through the housing 64 by the needle hub 70 in order to deliver the drug 72.

Figure 25:
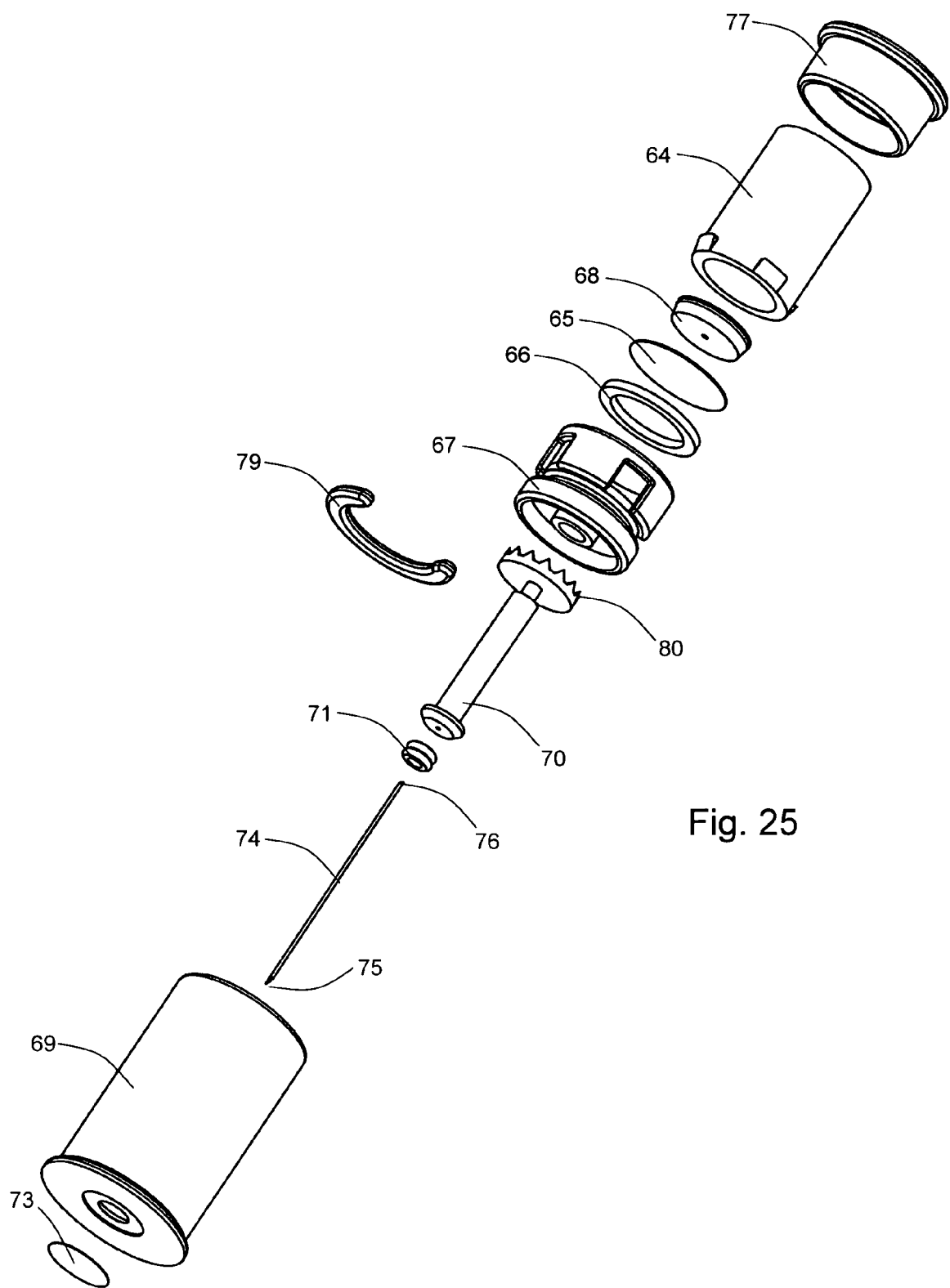
FIG. 25 is an exploded view of FIG. 21.

FIG. 25 shows an exploded view of FIG. 21.

Figures 26A, 26B, 26C, 26D:
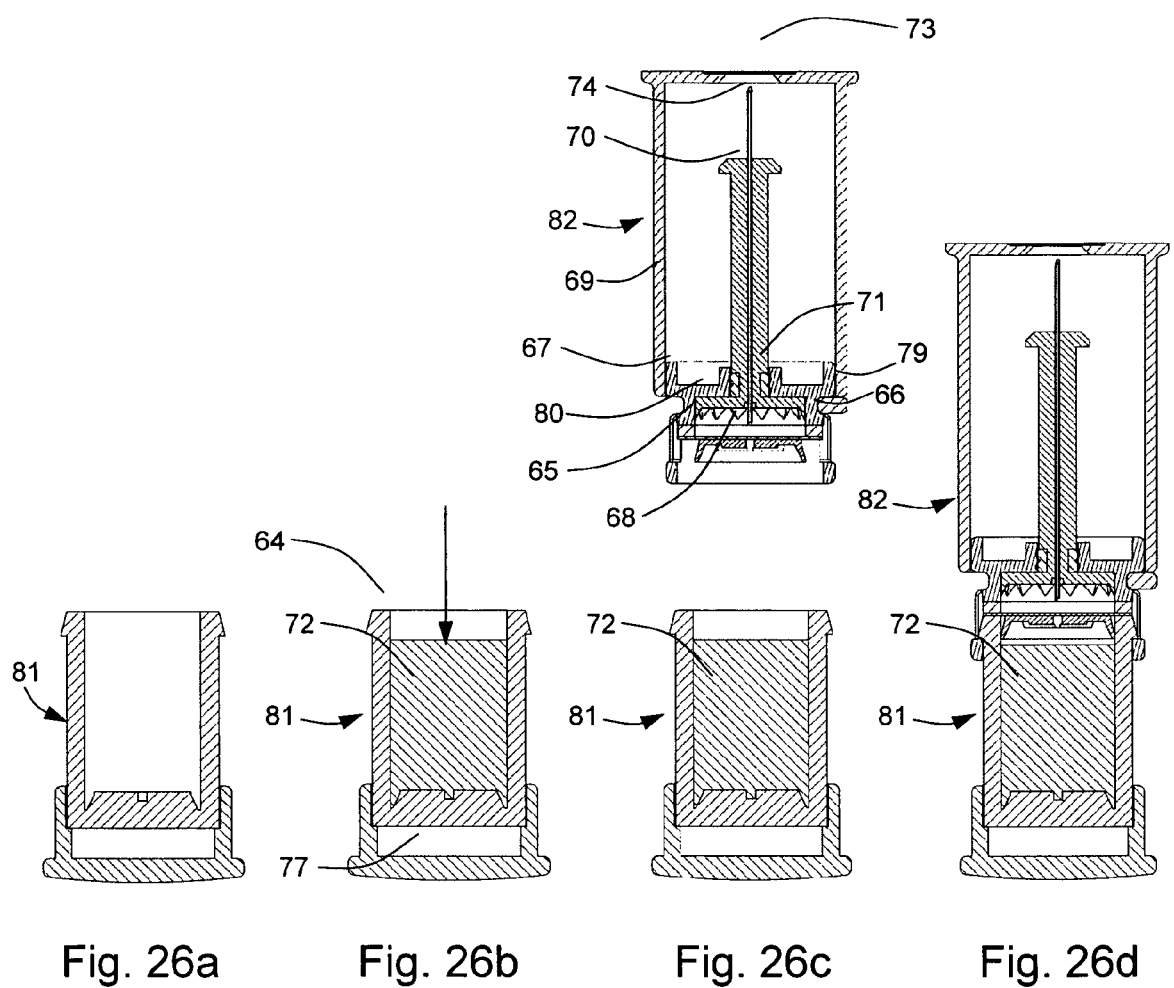
FIG. 26 shows the drug filling sequence for the invention described in FIG. 21.

FIGS. 26a to 26d show the filling sequence for FIG. 21. FIG. 26a shows the container portion 81 ready for filling. FIG. 26b shows the container portion 81 after it has been filled with drug 72. FIG. 26c shows the lid portion 82 in position above the container portion 81 ready for assembly. FIG. 26d shows the lid portion 82 and the container portion 81 assembled together with the drug 72.

As with the embodiment described with reference to FIG. 14, the lid portion 82 can be preassembled outside of the aseptic environment and then sterilised before being fixed to the container portion 81 using a push-fit connection or other suitable mechanical fastening.

The invention claimed is:

1. A drug dispensing device comprising:
a housing containing a drug to be dispensed, the housing having a first end defining a first opening;
a plunger, positioned within the housing, in contact with the drug;
a first sealing element providing a first closure seal across the first opening of the housing; and
a pusher initially located on an opposite side of the first seal to the plunger, wherein the pusher is operable to break the first closure seal and move the plunger within the housing to dispense the drug;
wherein the plunger does not form a closure seal with the housing, wherein a peripheral portion of the plunger in contact with a wall of the housing comprises a substantially non-elastomeric material, and wherein the plunger forms a cup seal with the housing.

2. The device according to claim 1, wherein the first closure seal is substantially gas impermeable.

3. The device according to claim 1, wherein the first closure seal is sufficient to maintain the drug in a sterile condition.

4. The device according to claim 1, wherein the plunger is not coated in a lubricant.

5. The device according to claim 1, wherein the plunger has only a single continuous contact ring in contact with the housing.

6. The device according to claim 1, wherein the plunger is moveable within the housing and has coefficient of friction with the housing of less than 0.3.

7. The device according to claim 1, wherein the plunger is moveable within the housing and has a coefficient of friction with the housing of less than 0.3 when neither the plunger nor the housing is lubricated with a lubricant.

8. The device according to claim 1, wherein the first sealing element comprises a laminated foil.

9. The device according to claim 8, wherein the laminated foil includes a layer of aluminum.

10. The device according to claim 1, wherein the first sealing element is welded to the housing.

11. The device according to claim 1, wherein the housing further comprises a second end defining a second opening and a second sealing element providing a second closure seal across the second opening, wherein movement of the plunger away from the first opening causes dispensing of the drug from the housing through the second opening.

12. The device according to claim 1, wherein the housing is formed primarily from a plastics material.

13. A drug dispensing device, comprising:
a housing containing a drug to be dispensed, the housing having a first end defining a first opening;
a plunger, positioned within the housing, in contact with the drug;
a first sealing element providing a first closure seal across the first opening of the housing; and
a pusher initially located on an opposite side of the first seal to the plunger, wherein the pusher is operable to break the first closure seal and move the plunger within the housing to dispense the drug;
wherein the plunger does not form a closure seal with the housing, wherein a peripheral portion of the plunger in contact with a wall of the housing comprises a substantially non-elastomeric material, and wherein the device comprises an auto-injector.

14. A drug dispensing device, comprising:
a housing containing a drug to be dispensed, the housing having a first end defining a first opening;
a plunger, positioned within the housing, in contact with the drug;
a first sealing element providing a first closure seal across the first opening of the housing; and
a pusher initially located on an opposite side of the first seal to the plunger, wherein the pusher is operable to break the first closure seal and move the plunger within the housing to dispense the drug;
wherein the plunger does not form a closure seal with the housing, wherein a peripheral portion of the plunger in contact with a wall of the housing comprises a substantially non-elastomeric material, and wherein the plunger is formed so that a component of the fluid pressure exerted by the drug during the delivery of the drug is directed towards a sealing interface between the plunger and the housing.

15. A primary drug container comprising:
a housing containing a drug, the housing having a first end defining a first opening;
a plunger, positioned within the housing, in contact with the drug; and
a first sealing element providing a first closure seal across the first opening of the housing, wherein the first sealing element is rupturable;
wherein the plunger does not form a closure seal with the housing, wherein a peripheral portion of the plunger in contact with a wall of the housing comprises a substantially non-clastomeric material, and wherein the plunger forms a cup seal with the housing.

16. The primary drug container according to claim 15, wherein the first closure seal is substantially gas impermeable.

17. The primary drug container according to claim 15, wherein the first closure seal is sufficient to maintain the drug in a sterile condition.

18. The primary drug container according to claim 15, wherein the plunger is not coated in a lubricant.

19. The primary drug container according to claim 15, wherein the plunger has only a single continuous contact ring in contact with the housing.

20. The primary drug container according to claim 15, wherein the plunger is moveable within the housing and has a coefficient of friction with the housing of less than 0.3.

21. A primary drug container, comprising:
a housing containing a drug, the housing having a first end defining a first opening:
a plunger, positioned within the housing, in contact with the drug; and
a first sealing element providing a first closure seal across the first opening of the housing, wherein the first sealing element is rupturable;
wherein the plunger does not form a closure seal with the housing, wherein a peripheral portion of the plunger in contact with a wall of the housing comprises a substantially non-elastomeric material, wherein movement of the plunger within the housing effects delivery of the drug, and wherein the plunger is formed so that a component of the fluid pressure exerted by the drug during delivery of the drug is directed towards a sealing interface between the plunger and the housing.

* * * * *

UNITED STATES PATENT AND TRADEMARK OFFICE
CERTIFICATE OF CORRECTION

| | | |
|---|---|---|
| PATENT NO. | : 8,632,504 B2 | Page 1 of 1 |
| APPLICATION NO. | : 13/202007 | |
| DATED | : January 21, 2014 | |
| INVENTOR(S) | : Matthew Young | |

It is certified that error appears in the above-identified patent and that said Letters Patent is hereby corrected as shown below:

In the Specification:

At column 2, line 55, delete "the the" and insert --the primary drug container. If the plunger ceases to move due to friction then the--.

At column 3, line 28, insert --using-- between "housing" and "heat".

At column 6, line 53, insert --using-- between "housing" and "heat".

Signed and Sealed this
Twenty-seventh Day of May, 2014

Michelle K. Lee
*Deputy Director of the United States Patent and Trademark Office*